US011305038B2

(12) United States Patent
Yoo et al.

(10) Patent No.: US 11,305,038 B2
(45) Date of Patent: Apr. 19, 2022

(54) VASCULAR CAST-BASED SCAFFOLDS AND METHODS OF MAKING THE SAME

(71) Applicant: WAKE FOREST UNIVERSITY HEALTH SCIENCES, Winston-Salem, NC (US)

(72) Inventors: James Yoo, Winston-Salem, NC (US); In Kap Ko, Clemmons, NC (US); Jennifer Huling, Winston-Salem, NC (US); Anthony Atala, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 595 days.

(21) Appl. No.: 15/747,352

(22) PCT Filed: Jul. 21, 2016

(86) PCT No.: PCT/US2016/043239
§ 371 (c)(1),
(2) Date: Jan. 24, 2018

(87) PCT Pub. No.: WO2017/019422
PCT Pub. Date: Feb. 2, 2017

(65) Prior Publication Data
US 2018/0214614 A1 Aug. 2, 2018

Related U.S. Application Data

(60) Provisional application No. 62/196,654, filed on Jul. 24, 2015.

(51) Int. Cl.
*A61L 27/56* (2006.01)
*A61K 35/44* (2015.01)
(Continued)

(52) U.S. Cl.
CPC .............. *A61L 27/56* (2013.01); *A61K 35/44* (2013.01); *A61L 27/20* (2013.01); *A61L 27/24* (2013.01);
(Continued)

(58) Field of Classification Search
CPC ...... A61L 27/56; A61L 27/3804; A61L 27/50; A61L 27/24; A61L 27/3826; A61L 27/3808; A61L 27/507
See application file for complete search history.

(56) References Cited

U.S. PATENT DOCUMENTS

2010/0196432 A1    8/2010   Feinberg et al.
2012/0179271 A1    7/2012   Liu et al.
(Continued)

FOREIGN PATENT DOCUMENTS

WO      2010096469 A2    8/2010

OTHER PUBLICATIONS

Lee, Biomimetic architectural design scaffolds and modulation of protein delivery for intestinal tissue engineering, Dissertation, University of California (2007). (Year: 2007).*
(Continued)

*Primary Examiner* — Kara D Johnson
(74) *Attorney, Agent, or Firm* — Nelson Mullins Riley & Scarborough LLP; Reza Mollaaghababa

(57) ABSTRACT

The present application relates to biomimetic three-dimensional (3D) scaffolds, constructs and methods of making the same. The three-dimensional scaffold can include a sacrificial internal cast and a durable external scaffold material, wherein the durable external scaffold material comprises a biocompatible material which completely surrounds the sacrificial internal cast and wherein the sacrificial internal
(Continued)

cast be removed to yield a branching 3D network of hollow, vessel-like tubes that substantially mimics a native tissue or organ.

21 Claims, 17 Drawing Sheets

(51) Int. Cl.
| | |
|---|---|
| *A61L 27/24* | (2006.01) |
| *A61L 27/38* | (2006.01) |
| *A61L 27/50* | (2006.01) |
| *A61L 27/52* | (2006.01) |
| *A61K 35/33* | (2015.01) |
| *A61K 35/34* | (2015.01) |
| *A61K 35/39* | (2015.01) |
| *A61K 35/407* | (2015.01) |
| *A61L 27/20* | (2006.01) |

(52) U.S. Cl.
CPC ....... *A61L 27/3804* (2013.01); *A61L 27/3808* (2013.01); *A61L 27/3821* (2013.01); *A61L 27/3826* (2013.01); *A61L 27/50* (2013.01); *A61L 27/507* (2013.01); *A61L 27/52* (2013.01); *A61K 35/33* (2013.01); *A61K 35/34* (2013.01); *A61K 35/39* (2013.01); *A61K 35/407* (2013.01); *A61L 2430/20* (2013.01); *A61L 2430/22* (2013.01); *A61L 2430/28* (2013.01); *A61L 2430/30* (2013.01)

(56) References Cited

U.S. PATENT DOCUMENTS

| | | |
|---|---|---|
| 2012/0190793 A1 | 7/2012 | Halter et al. |
| 2014/0234388 A1* | 8/2014 | Christ ................ A61K 33/38 |
| | | 424/423 |

OTHER PUBLICATIONS

Lee et al., Vasculature formation using three-dimensional cell printing technology. Proceedings of the 2010 IEEE 36th Annual Northeast Bioengineering Conference (NEBEC), New York, NY, 2010, pp. 1-2, doi: 10.1109/NEBC.2010.5458241. (Year: 2010).*

Lee, Biomimetic Architectural Design Scaffolds and Modulation of Protein Delivery for Intestinal Tissue Engineering, Dissertation, University of California (2007).

Huling et al., Fabrication of biomimetic vascular scaffolds or 3D tissue constructs using vascular corrosion cast, Acta Biomaterialia, (2016), 32:190-197.

International Search Report and Written Opinion dated Oct. 4, 2016 for International Application No. PCT/US2016/043239, 11 pages.

International Preliminary Report on Patentability dated Feb. 8, 2018 in related International Application No. PCT/US2016/043239, 10 pages.

European Search Report, 16831085.2, dated Feb. 28, 2019, 8 pages.

European Examination Report, 16831085.2, dated Apr. 20, 2020, 7 pages.

* cited by examiner

FIG. 5A 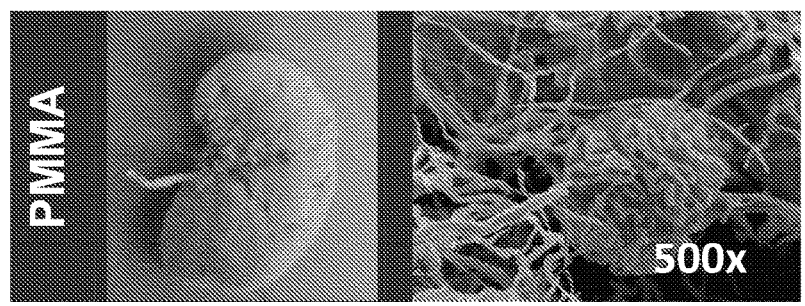 FIG. 5B
FIG. 5C 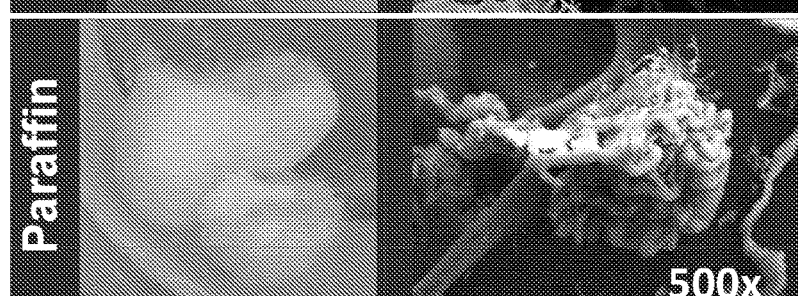 FIG. 5D
FIG. 5E 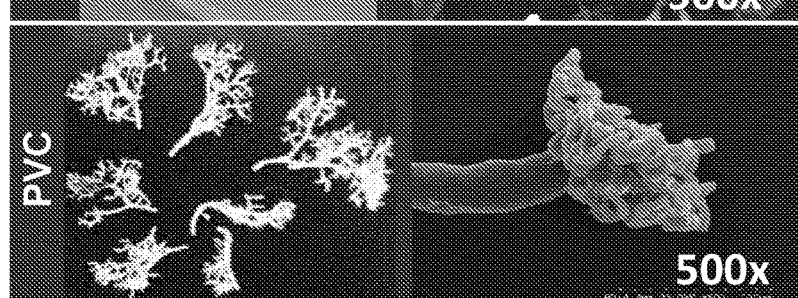 FIG. 5F
FIG. 5G 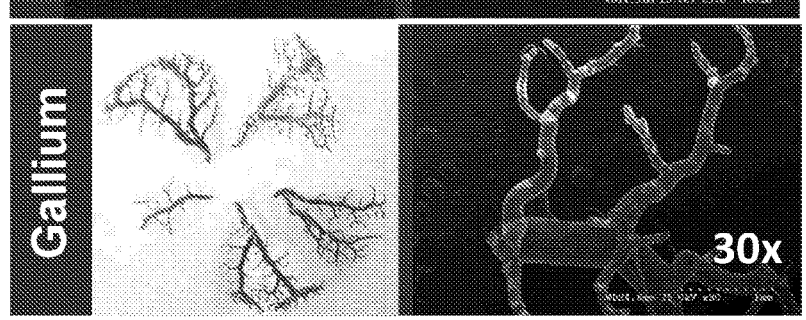 FIG. 5H
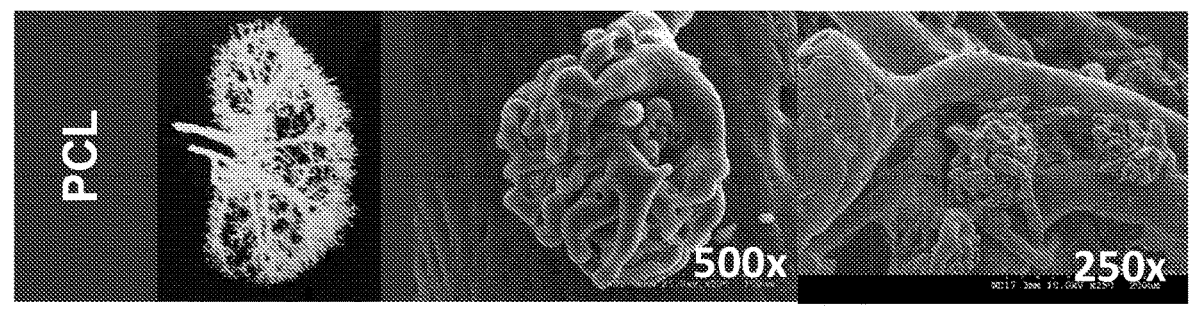
FIG. 5I        FIG. 5J        FIG. 5K FIG. 6C
FIG. 6D
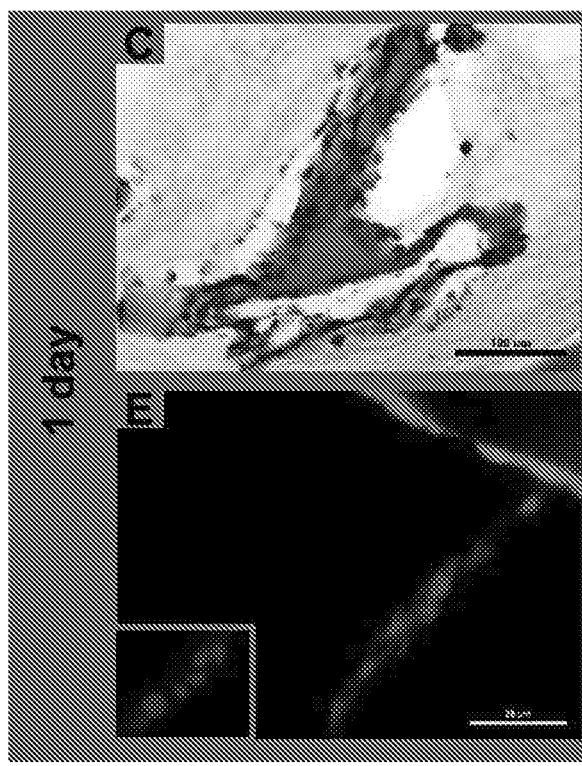
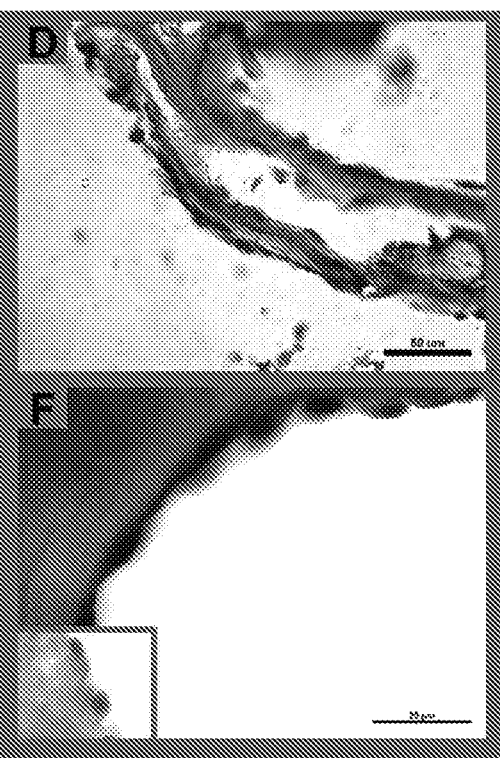
FIG. 6E
FIG. 6F FIG. 7A
FIG. 7C
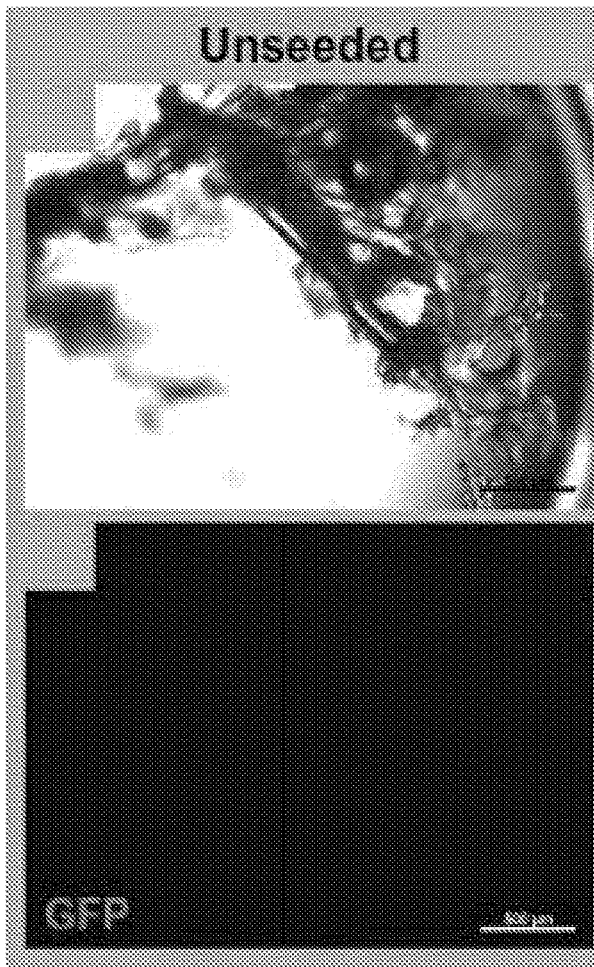
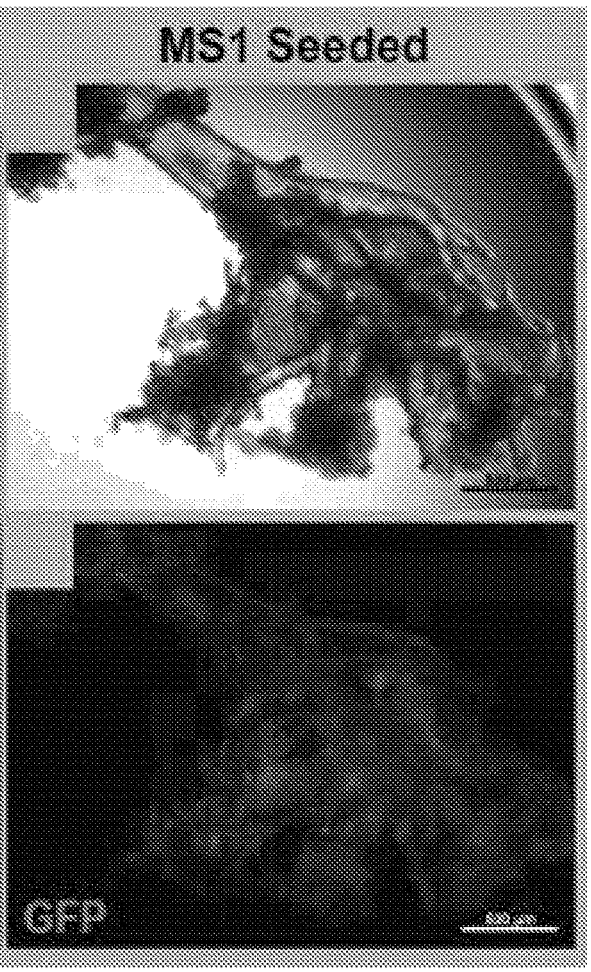
FIG. 7B
FIG. 7D

VASCULAR CAST-BASED SCAFFOLDS AND METHODS OF MAKING THE SAME

CROSS-REFERENCE TO RELATED APPLICATIONS

This application is a U.S. national stage filing under 35 U.S.C. § 371 of International Application No. PCT/US2016/043239 filed Jul. 21, 2016, which claims priority under 35 U.S.C. § 119(e) of U.S. Provisional Application Ser. No. 62/196,654, filed Jul. 24, 2015, the disclosures of which are herein incorporated by reference in their entireties.

BACKGROUND

There is significant clinical need for engineered replacements for solid tissues and organs. For example, volumetric loss of muscle due to trauma or surgery has few restorative treatment options. These treatments commonly lead to loss of function and long term impairment. Moreover, disease-related failure of whole solid organs has led to over 100,000 people current waiting for liver and kidney transplants, far exceeding the supply of donor organs. These examples illustrate the types of problems that the field of tissue engineering seeks to solve by creating implantable functional tissue constructs.

Each tissue type presents its own specific challenges, but the one challenge common to all large constructs is vascularization. All living tissue is vascularized in order to supply oxygen and nutrients and carry away waste. Cells generally need to be within 200 μm of an oxygen source to survive, placing tremendous constraints on construct design. Some thin engineered constructs can rely solely on vascular infiltration from the host following implantation, but large constructs will not survive, as the rate of host vessel ingrowth typically is less than 1 mm per day. Oxygen supply can also be limited during extended in vitro culture. Pre-vascularization of 3D volumetric constructs offers a solution to these challenges.

The aim of pre-vascularization of tissue constructs is to fabricate vessel-like structures for oxygen delivery throughout the tissue during in vitro culture. Pre-vascularized structures can greatly improve oxygen delivery in vitro, and integrate with host vasculature following implantation improving construct function in vivo. One strategy for achieving pre-vascularization is endothelial cell self-assembly into vessel-like structures in co-culture systems. However, the resulting vessels are often randomly arranged. To improve vascular efficiency, more directed control of vascular geometry should be considered. Recently, biofabrication and microfluidic techniques have been used to gain geometric control over in vitro vessel networks. See, for example, Hasan et al. "Microfluidic Techniques for the Development of 3D Vascularized Tissue," *Biomaterials* 35(26): 7308-7325 (August 2014).

Soft lithography can produce branching networks of vessel-like tubes that can be seeded with endothelial cells. These techniques can be applied as 2D patterns or they can be stacked or rolled to produce 3D constructs. While 6 μm structures can be created in this manner, the patterns were limited in complexity and had to be initially created in two dimensions. To overcome this limitation, 3D bioprinting of sacrificial materials in hydrogels has been developed to provide improved 3D spatial control, with resolution below 20 μm. Image-based micropatterning has been applied to hydrogels to provide biomimetic patterns to guide endothelial cell alignment. See, for example, Culver et al. "Three-dimensional Biomimetic Patterning in Hydrogels to Guide Cellular Organization," *Advanced Materials* 24(17):2344-2349 (Deerfield Beach Fla. May 2, 2012).

Unfortunately, these techniques are costly, and the design complexity of the resulting vessels is still quite limited. Therefore, challenges remain in the fabrication of complex and specialized vascular structures. Such structures could facilitate efficient cellular organization in vitro and accelerate host vascular integration in vivo.

SUMMARY

Methods of fabricating three-dimensional (3D) hollow vascular scaffolds are disclosed. The vascular scaffolds can provide a biomimetic microvascular architecture to facilitate pre-vascularization of engineered tissue constructs. The present application also relates to 3D biomimetic scaffolds formed by these methods, as well as the use of these scaffolds.

In one embodiment, the 3D scaffolds can be formed by perfusing natural tissue with a material that can fill a native tissue vasculature. Once the vasculature is filled, the perfused material is solidified and the surrounding natural tissue removed (e.g., by digestion) leaving a sacrificial vascular corrosion cast. The sacrificial cast is then coated with a durable external scaffold material, e.g., a biocompatible material that surrounds the sacrificial internal cast. When the durable scaffold material coating has set, the internal cast is sacrificed, e.g., by dissolving and/or melting the internal cast material, to yield a branching 3D network of hollow vessel-like tubes that substantially mimics the original vasculature of a native tissue or organ.

In another aspect, the present invention relates to a three-dimensional vascular scaffold formed by coating a sacrificial vascular cast with a durable external scaffold material, and then removing, e.g., by dissolving and/or melting and draining the sacrificial internal cast to leave behind a hollow vascular scaffold that can then be internally and/or externally seeded with cells, preferably endothelial cells or endothelial progenitor cells. The cells seeded within the hollow scaffold can be grown in vitro and/or in vivo to form a confluent cellular layer in order to vascularize a surrounding tissue construct.

For example, following (or concurrently with) seeding of the hollow scaffold, the scaffold can be surrounded by a culture of cells that will form a tissue construct around the scaffold. In one embodiment, the cell culture is a culture of muscle cells or muscle-derived cells or progenitor cells capable of differentiating into muscle cells. In another embodiment the cell culture is a culture of skeletal or smooth muscle cells. In other embodiments, the cell culture is a culture of parenchymal cells chosen to regenerate a particular organ. Possible parenchymal cell types include renal cells, hepatocytes, pancreatic islet cells or beta-cells, or cardiac smooth muscle cells.

In some embodiments, the cell culture can be applied to the seeded scaffold as a gel or hydrogel loaded with a volume of cells that will form the desired tissue or organ. For example, the methods of making the scaffolds and constructs can employ collagen hydrogels and a population of skeletal or smooth muscle cells.

In certain embodiments, the material that will form the sacrificial internal cast can be a polycaprolactone-based material, e.g., a solution containing 5% to about 30% w/v polycaprolactone. Polycaprolactone is advantageous because it is readily soluble in many organic solvents. In other embodiments, the sacrificial casting material can be a gallium-based material. The melting point of gallium is about 30° C. (Gallium can also be alloyed with other materials such a tin and/or indium to alter its melting point.)

The scaffolds and constructs described herein can be used for reconstruction or regeneration of numerous types of native tissue or organs. They type of tissue used to create the vascular corrosion cast will dictate the final structure of the scaffold, allowing for tissue-specific construct creation. For instance, the hollow scaffolds of the present invention can provide a renal vasculature, a gastrointestinal vasculature, a pulmonary vasculature, a cardiac vasculature, a hepatic vasculature, a splenic vasculature, a pancreatic vasculature, and/or a musculoskeletal vasculature. In other embodiments, the native tissue types or organs that can be replaced or augmented by the constructs of the present invention include lung, heart, stomach, small intestine, large intestine, gall bladder, kidney, and/or bladder.

BRIEF DESCRIPTION OF THE DRAWINGS

In FIG. 1B, the native tissue can be digested leaving an internal vascular corrosion cast. In FIG. 1C, the internal cast can be coated with a durable external scaffold material, followed by removal of the internal casting material, resulting in a hollow vascular scaffold of FIG. 1D. The hollow vascular scaffold can then be seeded with endothelial cells, e.g., by perfusing a solution containing endothelial or endothelial progenitor cells into the inside of the hollow vascular scaffold, as shown in FIG. 1E. The seeded scaffold and can be embedded in a myoblast-laden hydrogel, as shown in FIG. 1F, to form a 3D muscle construct (FIG. 1G).

FIG. 3A is an image of a vascular corrosion cast made by perfusing 10% polycaprolactone (PCL) (w/v) into a rat kidney. FIG. 3B is a scanning electron micrograph (SEM) (200×) showing the resulting PCL vascular casting. FIG. 3C is a further SEM image (250×) of the PCL casting showing casting of glomerular capillaries. FIG. 3D is an image of a vascular corrosion cast made by perfusing gallium into a rat kidney. FIG. 3E is a scanning electron micrograph (SEM) (30×) showing the resulting gallium vascular casting and FIG. 3F is another SEM (150×) of microvascular structures in a gallium casting.

FIG. 4A is a scanning electron micrograph showing the 3D branching architecture of a durable collagen vascular scaffold. FIG. 4B is another scanning electron micrograph showing the 3D branching architecture of a durable collagen vascular scaffold. FIG. 4C is a further scanning electron micrograph showing the 3D branching architecture of a durable collagen vascular scaffold including a hollow inlet vessel (dashed line). FIG. 4D is an image of H&E staining of a durable collagen vascular scaffold showed long vessels cut longitudinally. FIG. 4E is another image of H&E staining of a durable collagen vascular scaffold showed hollow vessel cross-sections throughout the scaffold. FIG. 4F is likewise an image of H&E staining of a durable collagen vascular scaffold showed hollow vessel cross-sections. FIG. 4G is an image of a collagen cast with perfused dye showed continuous and connected structures. FIG. 4H is another image of a collagen cast with perfused dye showed continuous and connected structures. FIG. 4I is a further image of a collagen cast with perfused dye showed continuous and connected structures. (In each of FIGS. 4G-4I, arrows indicate progress of dye).

FIGS. 5A-5K illustrate gross and SEM images of Batson #17 (PMMA), paraffin, PVC, gallium and PCL vascular corrosion casts.

FIGS. 6A-6G illustrate maintenance of endothelialization of vascular scaffold within a 3D culture. FIGS. 6A and 6B illustrate seeded vascular scaffolds that were embedded in collagen hydrogels and fixed immediately. FIGS. 6C-6F illustrate seeded vascular scaffolds that were embedded in collagen hydrogels and fixed after 24 hours in culture. FIG. 6G illustrate a seeded vascular scaffold that was embedded in collagen hydrogels and fixed after 7 days in culture with renal cells.

FIGS. 7A-7D illustrate endothelialization of a vascular scaffold. Collagen-based vascular scaffolds were seeded with MS1 cells and cultured for 24 h. Unseeded scaffolds (FIG. 7A, bright field, 40×, scale: 500 µm) showed no visible GFP autofluorescence (FIG. 7B, 40×, scale: 500 µm) while seeded scaffolds (FIG. 7C, bright field, 40×, scale: 500 µm) showed endogenous expression of GFP in live cells and demonstrated complete and uniform MS1 coverage (FIG. 7D, 40×, scale: 500 µm).

DETAILED DESCRIPTION

Figure 1A:
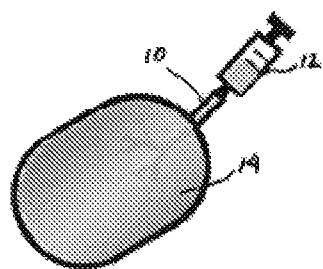
FIGS. 1A-G schematically illustrate the methods described herein. In an initial step, shown in FIG. 1A, sacrificial internal casting material can be perfused into native vasculature tissue.

The present application relates to biomimetic three-dimensional (3D) scaffolds, constructs and methods of making the same. In one aspect, the invention relates to a method of creating a biomimetic three-dimensional vascular scaffold comprising the steps of perfusing a sacrificial internal casting composition in the native vasculature of a tissue or organ, allowing the sacrificial internal casting composition to solidify within the native vasculature, digesting the native tissue surrounding vasculature casting, thereby creating a solid cast of the native vasculature, coating the solid cast with a biocompatible scaffold material, and removing the sacrificial internal vascular cast, thereby creating a biomimetic three-dimensional vascular scaffold.

In embodiments described below, the three-dimensional hollow scaffold is a biocompatible material in the shape of (e.g., a durable external cast of) a portion of native vasculature that is formed by perfusing a sacrificial internal casting composition into a tissue vasculature; solidifying the sacrificial internal casting composition within the native vasculature; digesting the native vasculature, thereby creating a solid cast of the native vasculature; and coating the solid cast with a biocompatible outer scaffold material. The sacrificial internal cast substantially mimics the vasculature space in a native tissue or organ.

As used herein, a "sacrificial internal cast" or "internal cast" can comprise any material or composition that is removable (e.g., dissolvable, meltable) under certain conditions. As described herein, under certain conditions, a sacrificial internal cast can harden or solidify. For example, the sacrificial internal cast can solidify after being partially or completely perfused into the vasculature of a tissue specimen or organ. In a fluid state, the perfused material can form the sacrificial internal cast and take the three-dimensional shape of the tissue or organ. Perfusion through a tissue or organ system results in the sacrificial internal cast to substantially mimic that tissue or organ system (i.e., biomimetic). Changing the certain conditions allows the sacrificial internal cast to be removed (e.g., dissolved or melted).

The sacrificial internal cast (e.g., casting composition) is configured to be removed. In some embodiments, the sacrificial internal cast can be removed by dissolving the sacrificial internal cast in a solution (e.g., an organic solvent). In other embodiments the sacrificial internal cast or casting composition can be removed by heating to liquefy the composition. The conditions under which the sacrificial internal cast can be removed can include other physical or chemical actions, as well. For example, a physical or chemical action can include, but is not limited to, changes in temperature (e.g., melting point), pressure, enzymatic digestion or solubility.

In certain embodiments, the sacrificial internal cast can comprise polycaprolactone (PCL). In some embodiments, polycaprolactone can be perfused as an acetone solution containing about 1%, about 5%, about 10%, about 15%, about 20%, about 25%, about 30%, about 40%, about 50%, or greater than about 50% w/v PCL. In some embodiments, PCL can comprise about 1 to about 50%, about 2 to about 40%, about 3 to about 30%, about 4 to about 20%, or about 5 to about 15% w/v of the solution.

In another embodiment, the sacrificial internal cast comprises gallium or a gallium alloy. Other temperature sensitive material may be used, for example paraffin or other types of wax with melting points below approximately 60° C. or gelatin. In other embodiments, polyvinyl chloride or temperature-dependent polymers (e.g., Pluronic® F-127, a surfactant polyol) can be used as the sacrificial casting material.

The tissue or organ system can comprise any native hollow structure through which the sacrificial internal casting composition can be perfused. For example, a native tissue or organ system comprising hollow structures can comprise a vasculature. The vasculature can comprise any vasculature in an animal (e.g., a mammal), such as, for example, a renal vasculature, a gastrointestinal vasculature, a nervous system (e.g., CNS) vasculature, a pulmonary vasculature, a cardiac vasculature, a hepatic vasculature, a splenic vasculature, a pancreatic vasculature, and/or a musculoskeletal vasculature.

As used herein, a "durable scaffold material" or "vascular scaffold" can comprise any material that can surround the internal cast. Preferably, the durable scaffold material cannot be removed (e.g., dissolved, melted, etc.) when exposed to the same or similar conditions as the sacrificial internal cast. As described herein, the durable scaffold material can completely surround the sacrificial internal cast.

The durable scaffold material is preferably formed of a biocompatible material. In one embodiment, the biocompatible material comprises a naturally occurring material (e.g., collagen). In one embodiment, the biocompatible material comprises a synthetic material. In some embodiments wherein the biocompatible material comprises collagen, the collagen can comprise about 1%, about 5%, about 10%, about 15%, about 20%, about 25%, about 30%, about 40%, about 50%, or greater than about 50% w/v collagen. In some embodiments, the collagen can comprise about 1 to about 50%, about 2 to about 40%, about 3 to about 30%, about 4 to about 20%, or about 5 to about 15%. In some embodiments it can be preferable to select a scaffold material that will biodegrade or be absorbed over time.

The biocompatible scaffold material can comprise a naturally occurring material. Examples of biocompatible, naturally-occurring materials include, but are not limited to, amino acids, peptides, denatured peptides such as gelatin from denatured collagen, polypeptides, proteins, carbohydrates, lipids, glycoproteins, lipoproteins, glycolipids, glycosaminoglycans, proteoglycans, and chitin or its derivative, chitosan. In one embodiment, the biocompatible compound is an extracellular matrix material, including but not limited to collagen, fibrin, elastin, laminin, fibronectin, hyaluronic acid, chondroitin 4-sulfate, chondroitin 6-sulfate, dermatan sulfate, heparin sulfate, heparin, and keratan sulfate, and proteoglycans or a combination of one or more of these materials. These materials may be isolated from humans or other animals or cells. A preferred natural compound is collagen. Examples of collagen include, but are not limited to collagen I, collagen II, collagen III, collagen IV, collagen V, collagen VI, collagen VII, collagen VIII, collagen IX, and collagen X. Another preferred natural compound is elastin. Elastin fibers are responsible for the elastic properties of several tissues. Elastin is found, for example, in skin, blood vessels, and tissues of the lung where it imparts strength, elasticity and flexibility.

In some embodiments, the biocompatible material can comprise a synthetic material alone or in conjunction with a natural material. One class of synthetic materials are biocompatible synthetic polymers. Such polymers include, but are not limited to, poly(urethanes), poly(siloxanes) or silicones, poly(ethylene), poly(vinyl pyrrolidone), poly(2-hydroxy ethyl methacrylate), poly(N-vinyl pyrrolidone), poly (methyl methacrylate), poly(vinyl alcohol) (PVA), poly (acrylic acid), poly(vinyl acetate), polyacrylamide, poly (ethylene-co-vinyl acetate), poly(ethylene glycol), poly (methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), poly(vinyl acetate), polyvinylhydroxide, poly(ethylene oxide) (PEO) and polyorthoesters or any other similar synthetic polymers that may be developed that are biologically compatible.

The durable scaffold material can act as a scaffold during cell culture. The scaffold, for example, can be seeded with a population of cells. Populations of cells can be seeded directly onto the vascular scaffold internally and/or externally. The seeded scaffold can be further surrounded by a gel-based construct containing cells. As described herein, one population of cells suitable for seeding directly on the vascular scaffold comprises endothelial cells. In some embodiments, the population of cells suitable for growth around the durable cast can comprise skeletal or smooth muscle cells. In other embodiments, the population of cells can comprise fibroblasts. In yet other embodiments, the population of cells comprises progenitor cells. In some embodiments, the population of cells comprise 1 or more (e.g., 2, 3, 4, 5 or 6) types of cells. Possible cell types include renal cells, hepatocytes, pancreatic islet cells or beta-cells, or smooth muscle cells.

In some embodiments, the present invention relates to a three-dimensional vascular scaffold comprising a sacrificial internal cast and a durable scaffold material, wherein the durable scaffold material comprises a biocompatible material which completely surrounds the sacrificial internal cast and wherein the sacrificial internal cast substantially mimics a native vasculature of a tissue or organ. The sacrificial internal cast can be retained as a part of the scaffold up until its time of intended use. When the scaffold is needed, the sacrificial internal cast can be removed.

The present invention also encompasses methods of creating a biomimetic three-dimensional vascular scaffold by perfusing a sacrificial internal casting composition into a native vasculature of a tissue or organ, allowing the sacrificial internal casting composition to solidify within the native vasculature, digesting the native vasculature of the tissue or organ, thereby creating a solid cast of the native vasculature, coating the solid cast with a biocompatible material, and removing the sacrificial internal vascular cast, thereby creating a biomimetic three-dimensional vascular scaffold.

Any tissue or organ that can be perfused with a sacrificial casting material can be used. The tissue or organ used to create the vascular cast can be from an autologous or allogenic source. Alternatively, the tissue can also be xenogenic, derived from a mammalian species that are different from the subject. For example, tissue cells can be derived from mammals such as monkeys, dogs, cats, mice, rats, cows, horses, pigs, goats and sheep. When creating the finished tissue construct, the type used to create the sacrificial cast and the parenchymal cell type incorporated into the construct can be from the same organ or different organs.

The cells to be seeded (e.g., externally and/or internally) upon the scaffold are preferably cells obtained from the subject's own tissue. A biopsy can be obtained by using a biopsy needle under a local anesthetic, which makes the procedure quick and simple. The small biopsy core of the isolated tissue can then be expanded and cultured to obtain the tissue cells. In some cases, progenitor cells of various types can be isolated from tissue, blood, umbilical cord or body fluids. The progenitor cells can be expanded and differentiated in vitro. Cells from relatives or other donors of the same species can also be used with appropriate immunosuppression.

Methods for the isolation and culture of cells are discussed by Freshney, Culture of Animal Cells. A Manual of Basic Technique, 2d Ed., A. R. Liss, Inc., New York, 1987, Ch. 9, pp. 107-126. Cells useful in seeding the scaffolds may be isolated using techniques known to those skilled in the art. For example, the tissue can be cut into pieces, disaggregated mechanically and/or treated with digestive enzymes and/or chelating agents that weaken the connections between neighboring cells making it possible to disperse the tissue into a suspension of individual cells without appreciable cell breakage. If necessary, enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, and dispase. Mechanical disruption can also be accomplished by a number of methods including, but not limited to, scraping the surface of the tissue, the use of grinders, blenders, sieves, homogenizers, pressure cells, or insonators.

Cell types include, but are not limited to, progenitor cells isolated from the peripheral blood or bone that can be induced to differentiate into different cells, stem cells, committed stem cells, and/or differentiated cells may be used. Also, depending on the type of tissue or organ being made, specific types of committed stem cells can be used. For instance, myoblast cells can be used to build various muscle structures. Other types of committed stem cells can be used to make organs or organ-like tissue such as heart, kidney, liver, pancreas, spleen, bladder, ureter and urethra. Other cells include, but are not limited to, endothelial cells, skeletal muscle cells, smooth muscle cells, fibroblasts, osteoblasts, myoblasts, neuroblasts, fibroblasts, glioblasts, germ cells, hepatocytes, chondrocytes, keratinocytes, cardiac muscle cells, connective tissue cells, epithelial cells, endothelial cells, hormone-secreting cells, cells of the immune system, neurons, cells from the heart, kidney, liver, pancreas, spleen, bladder, ureter and urethra, and the like. In some embodiments it is unnecessary to pre-select the type of stem cell that is to be used, because many types of stem cells can be induced to differentiate in an organ specific pattern once delivered to a given organ. For example, a stem cell delivered to the liver can be induced to become a liver cell simply by placing the stem cell within the biochemical environment of the liver.

Examples also include cells that have been genetically engineered, transformed cells, and immortalized cells. One example of genetically engineered cells useful in the present invention is a genetically engineered cell that makes and secretes one or more desired molecules. When the engineered vascular scaffolds comprising genetically engineered cells are implanted in an organism, the molecules produced can produce a local effect or a systemic effect, and can include the molecules identified above as possible substances.

Isolated cells can be cultured in vitro to increase the number of cells available for seeding on the vascular scaffold. To prevent an immunological response after implantation of the scaffold, the subject may be treated with immunosuppressive agents such as, cyclosporin or FK506.

Isolated cells can be transfected with a nucleic acid sequence. Useful nucleic acid sequences may be, for example, genetic sequences which reduce or eliminate an immune response in the host. For example, the expression of cell surface antigens such as class I and class II histocompatibility antigens may be suppressed. In addition, transfection could also be used for gene delivery. Cells can be transfected with specific genes prior to seeding onto the biocompatible substitute. Thus, the cultured cells can be engineered to express gene products that would produce a desired protein that helps ameliorate a particular disorder.

The cells grown on the vascular scaffolds described herein can also be genetically engineered to produce gene products beneficial to implantation, e.g., anti-inflammatory factors, e.g., anti-GM-CSF, anti-TNF, anti-IL-1, and anti-IL-2. Alternatively, the cells can be genetically engineered to "knock out" expression of native gene products that promote inflammation, e.g., GM-CSF, TNF, IL-1, IL-2, or "knock out" expression of MHC in order to lower the risk of rejection. Alternatively, the cells can be genetically engineered to "knock in" expression of one or more gene products.

Growth factors and regulatory factors can be added to enhance, alter or modulate proliferation and cell maturation and differentiation of the cells. The growth and activity of cells can be affected by a variety of growth factors such as growth hormone, somatomedins, colony stimulating factors, erythropoietin, epidermal growth factor, hepatic erythropoietic factor (hepatopoietin), and like. Other factors which regulate proliferation and/or differentiation include prostaglandins, interleukins, and naturally-occurring chalones.

The vascular scaffolds of the invention can be used in a variety of applications. For example, the scaffolds can be implanted into a subject to replace or augment existing vasculature. The subject can be monitored after implantation, for amelioration of a disorder.

In some embodiments, the methods of making the vascular scaffolds and constructs further comprise embedding the three-dimensional scaffold or construct in a hydrogel. In some embodiments, the hydrogel comprises a population of cells. In some embodiments, the population of cells comprises skeletal or smooth muscle cells. For example, the vascular scaffolds can also test the in vitro functionality of a skeletal muscle construct. Skeletal muscle tissue is appropriate to test the functionality of the microvascular scaffolds described herein, because muscle tissue is highly sensitive to hypoxia and nutrient deprivation due to its high metabolic rate.

In some embodiments, the gel (e.g., hydrogel) solidifies after the three-dimensional vascular scaffold is embedded. Hydrogel compositions can include, without limitation, for example, poly(esters), poly(hydroxy acids), poly(lactones), poly(amides), poly(ester-amides), poly(amino acids), poly(anhydrides), poly(ortho-esters), poly(carbonates), poly(phosphazines), poly(thioesters), polysaccharides and mixtures thereof. Furthermore, the hydrogel compositions can also include, for example, a poly(hydroxy) acid including poly(alpha-hydroxy) acids and poly(beta-hydroxy) acids. Such poly(hydroxy) acids include, for example, polylactic acid, polyglycolic acid, polycaproic acid, polybutyric acid, polyvaleric acid, and copolymers and mixtures thereof.

In some embodiments, cells are mixed with one or more suitable gels for administration. Suitable gels that can be used in the present invention include, but are not limited to, agars, collagen, fibrin, hydrogels, etc. Besides gels, other support compounds can also be utilized. Extracellular matrix analogs, for example, can be combined with support gels to optimize or functionalize the gel. One or more growth factors may also be introduced into the cell suspensions.

Figure 1B:
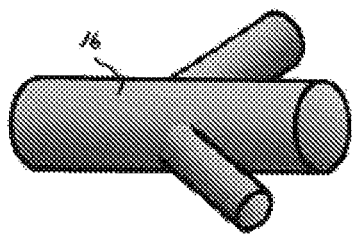
Figure 1C:
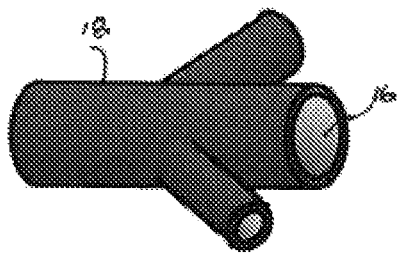
Figure 1D:
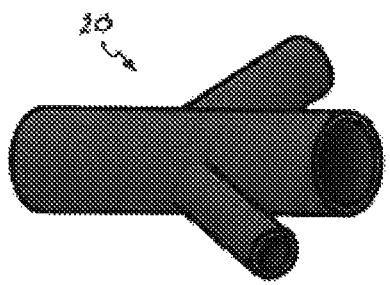
Figure 1E:
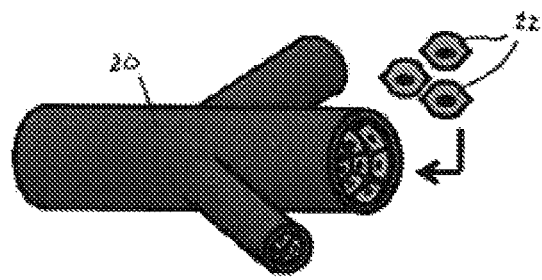
Figure 1F:
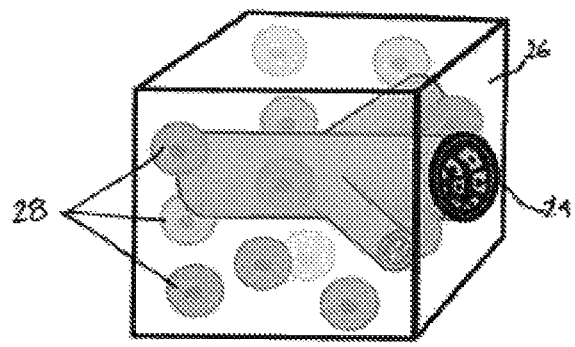
Figure 1G:
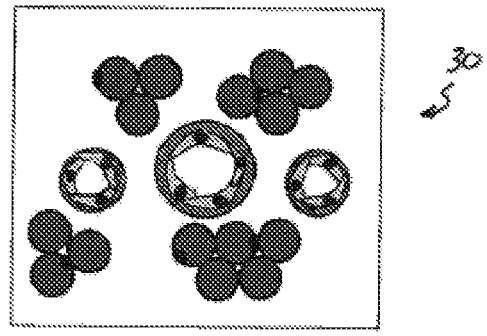

One method of practicing the invention is schematically shown in FIGS. 1A-1G. In an initial step, shown in FIG. 1A, a sacrificial internal casting material 10 can be perfused via syringe 12 into a vascularized tissue 14 obtained from an autologous, allogenic or xenogenic source. In FIG. 1B, the native tissue 14 can be digested leaving a vascular internal corrosion cast 16. In FIG. 1C, the internal cast can be coated with a durable external scaffold material 18, followed by removal of the internal casting material, resulting in a hollow vascular scaffold 20 of FIG. 1D. The internal surface of the hollow vascular scaffold 20 can then be seeded with endothelial cells 22, e.g., by perfusing a solution containing endothelial or endothelial progenitor cells into the inside of the hollow vascular scaffold, as shown in FIG. 1E. The seeded scaffold 24 and can be embedded in a hydrogel 26 containing myoblasts or other scaffold-seeding cells 28, as shown in FIG. 1F, to form a 3D muscle construct 30 (FIG. 1G).

Figure 2A:
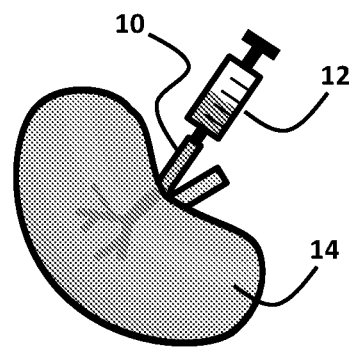
FIGS. 2A-2G illustrate another embodiment of the methods described herein to form a 3D kidney construct.
Figure 2B:
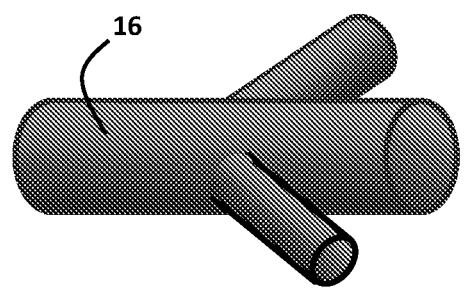
Figure 2C:
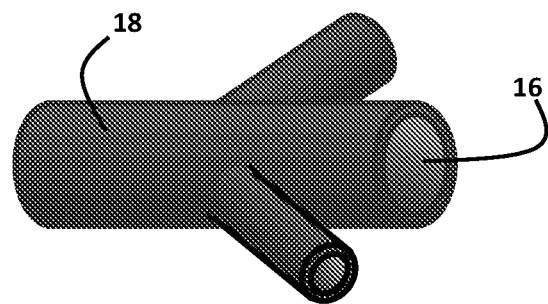
Figure 2D:
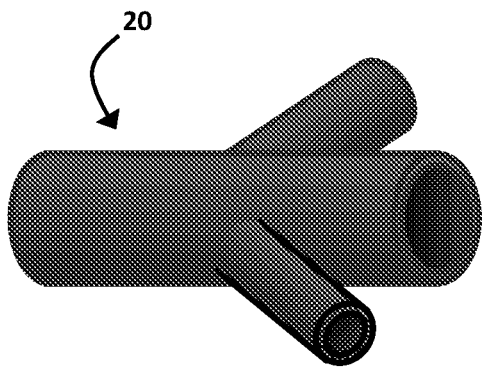
Figure 2E:
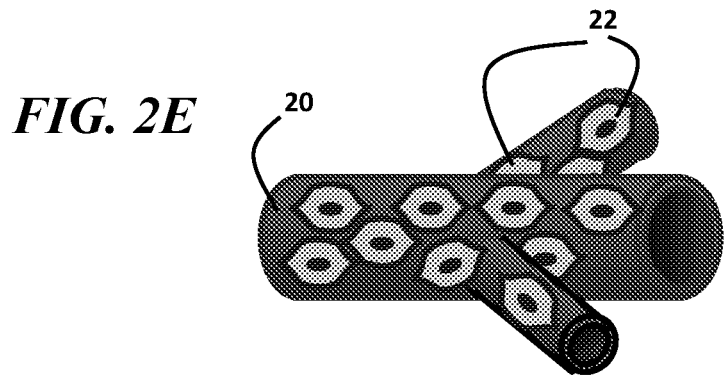
Figure 2F:
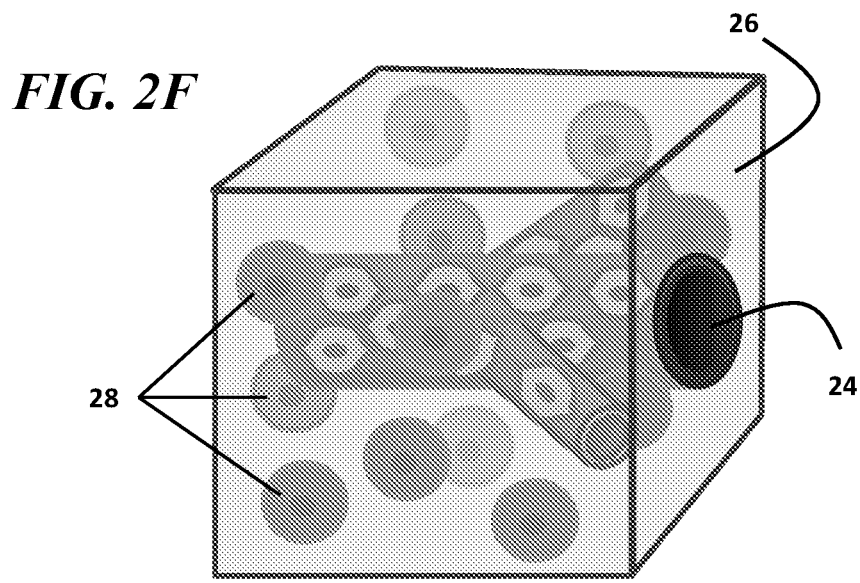
Figure 2G:
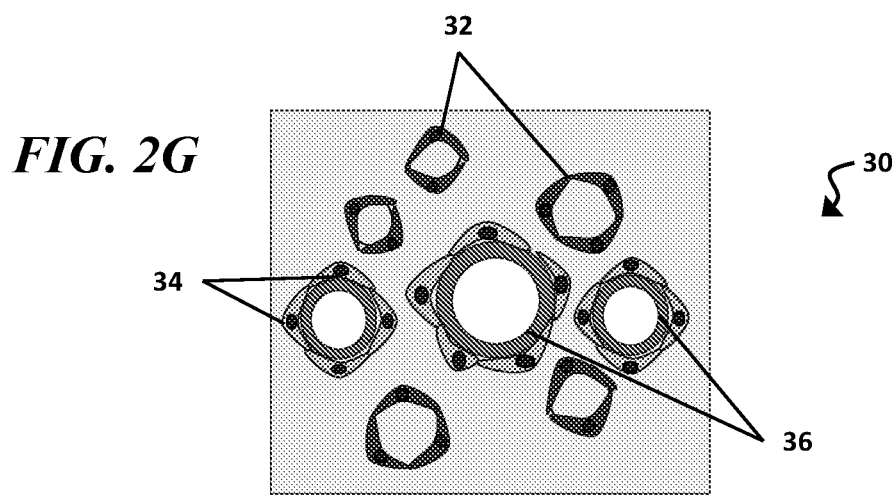

Another embodiment of the method described herein is schematically shown in FIGS. 2A-2G. Similar to steps illustrated in FIGS. 1A-1D, an initial step, shown in FIG. 2A, a sacrificial internal casting material 10 can be perfused via syringe 12 into a vascularized tissue 14 (e.g., a kidney) obtained from an autologous, allogenic or xenogenic source. In FIG. 2B, the native tissue 14 can be digested (e.g., using NaOH) leaving a vascular internal corrosion cast 16. In FIG. 2C, the internal cast 16 can be coated with a durable external scaffold polymer material 18, followed by removal of the internal casting material 16, resulting in a hollow vascular scaffold 20 of FIG. 2D. The external surface of the hollow vascular scaffold 20 can then be seeded with endothelial cells 22, e.g., by perfusing a solution containing endothelial (e.g., MS-1 cells) or endothelial progenitor cells on the outside of the hollow vascular scaffold, as shown in FIG. 2E. The seeded vascular scaffold 24 and can be embedded in a hydrogel 26 containing myoblasts, primary renal cells or other scaffold-seeding cells 28, as shown in FIG. 2F, to form a 3D construct 30 (FIG. 2G). Constructs can be cultured to allow for self-assembly of renal structures 32 among the endothelial lined vessels 34.

Other embodiments and used of the invention will be apparent to those skilled in the art from consideration of the specification and practice of the invention disclosed herein. All U.S. patents and other references noted herein for whatever reason are specifically incorporated by reference. The specification and examples should be considered exemplary only with the true scope and spirit of the invention indicated by the following claims.

The following examples are provided for further illustration of various aspects of the present teachings, and are not necessarily intended to indicate optimal ways of practicing the invention.

EXAMPLES 1 AND 2

Vascular corrosion casting techniques have been traditionally used for analysis of the morphology and architecture of normal vascular structures. The technique has also been used for the identification of developmental morphogenetic changes, and identification of morphological differences in tissue architecture between normal and disease states. Current standard corrosion casting materials are polymethyl methacrylate (PMMA) or polyurethane. While PMMA and polyurethane make durable and precise vascular casts, they are not appropriate as sacrificial materials, since they cannot be easily dissolved.

Initial investigation into appropriate sacrificial casting materials yielded two candidates: polycaprolactone (PCL) and gallium. These were chosen because PCL dissolved in many organic solvents (e.g., acetone) and gallium has an extremely low melting temperature. In Example 1, a solution of 10% PCL in acetone was perfused through healthy rat kidneys and processed as a normal vascular cast. In Example 2, melted gallium was perfused separately through healthy rat kidneys and also processed as a normal vascular cast. Kidney tissue was used due to its very complex vascular architecture.

Figure 3A:
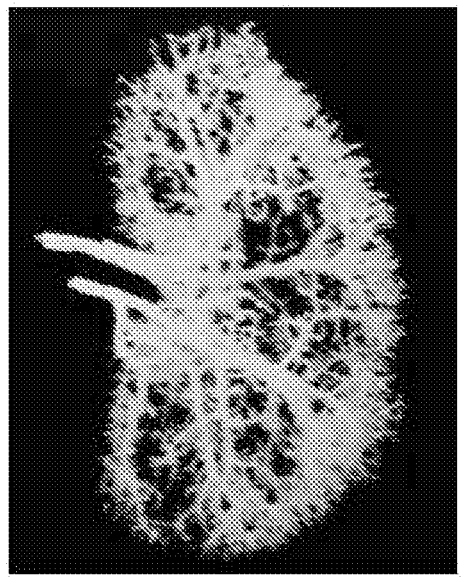
FIGS. 3A-3F further illustrate the construction of vascular corrosion casts according to the invention.

In Example 1, using PCL, the resulting casts showed uniform vascular representation of the entire organ (see FIG. 3A). Scanning electron microscope (SEM) evaluation of the PCL casts showed preservation of fine capillary structure, and visible glomeruli (see FIGS. 3B and 3C).

Figure 3B:
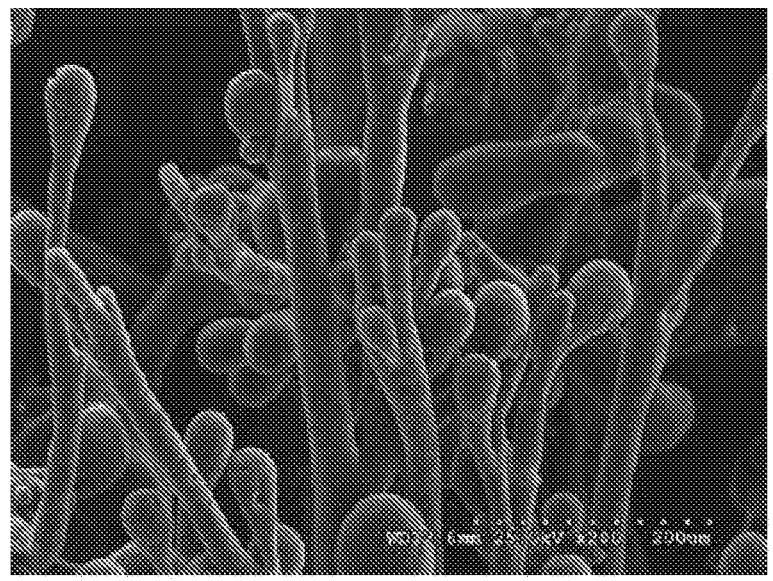
Figure 3C:
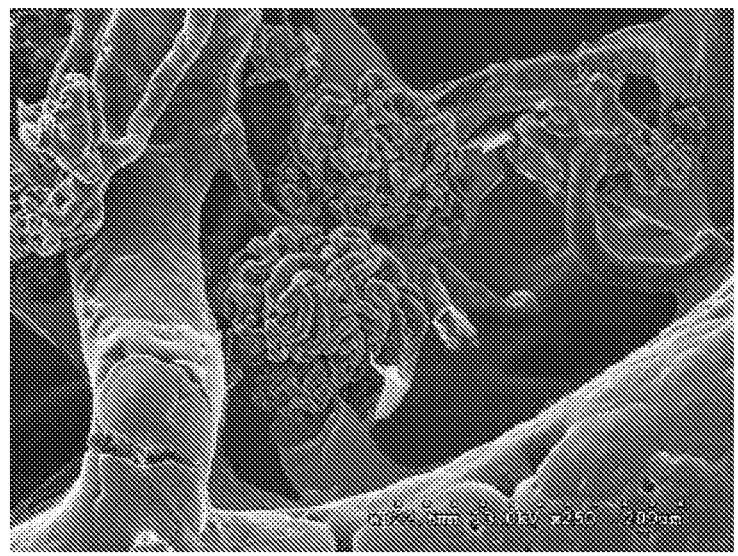
Figure 3D:
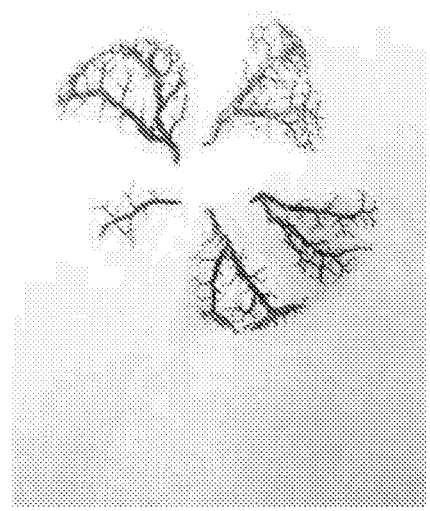
Figure 3E:
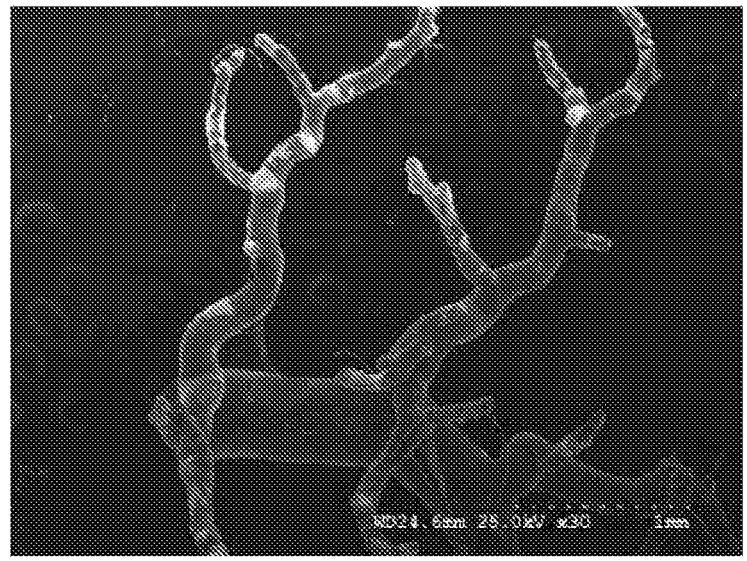
Figure 3F:
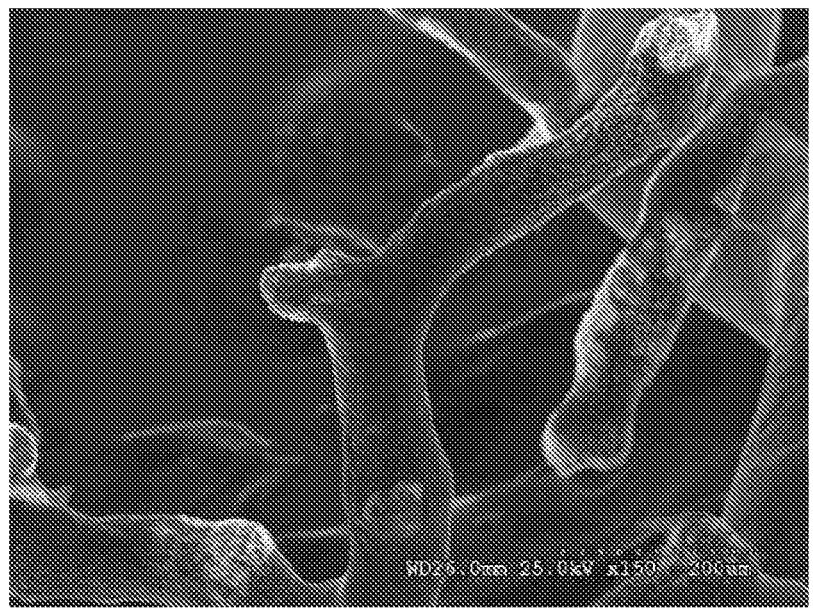

In Example 2, using gallium, the resulting casts again showed uniform vascular representation of the entire organ (see FIG. 3D). Gallium produced a branched vascular cast, but formed incomplete microvascular structures (see FIGS. 3E and 3F).

Figure 4A:
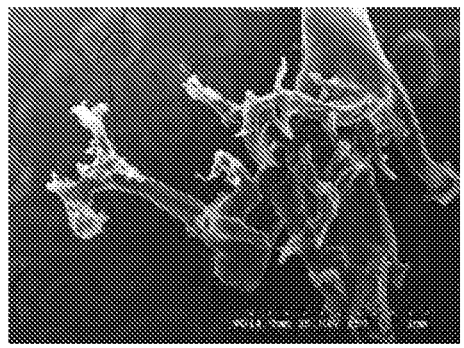
FIGS. 4A-4I illustrate collagen vascular scaffolds prepared from sacrificial corrosion casts have hollow, branching structures.
Figure 4B:
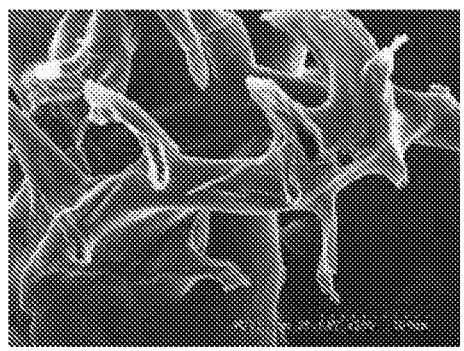
Figure 4C:
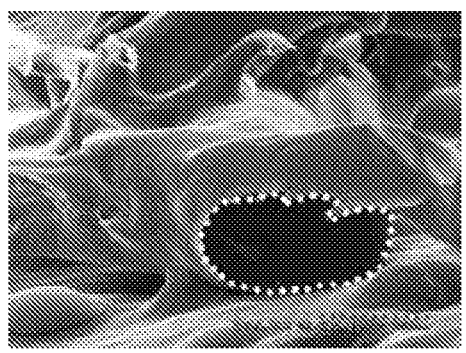
Figure 4D:
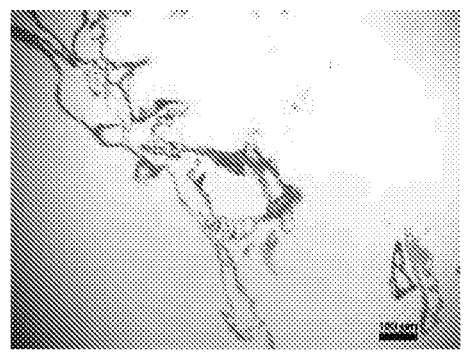
Figure 4E:
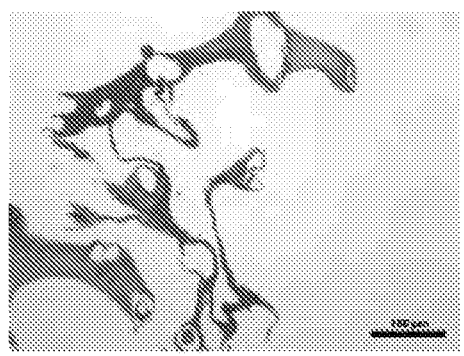
Figure 4F:
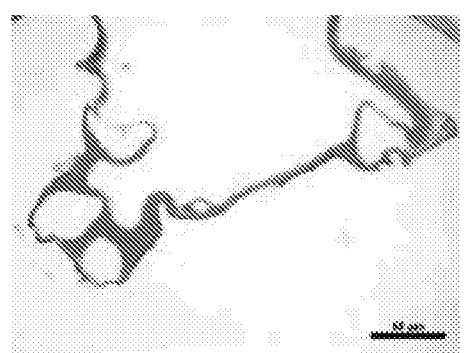
Figure 4G:
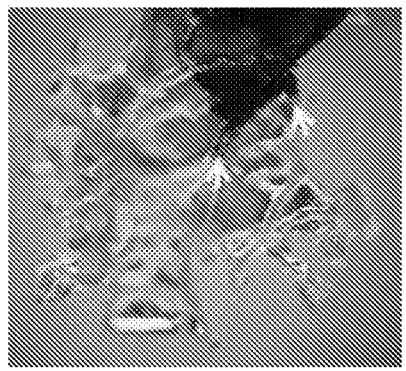
Figure 4H:
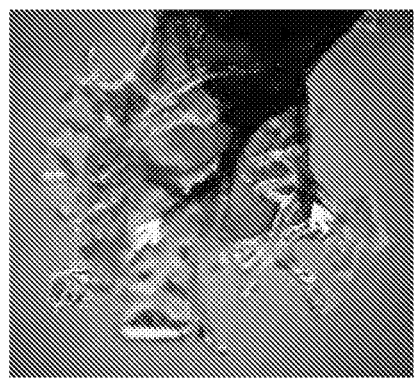
Figure 4I:
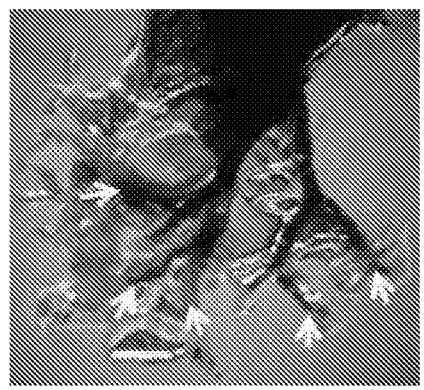

To examine whether hollow structures could be created by removing the internal, vascular cast (see FIGS. 1D and 2D), the PCL casts were coated with an external, durable scaffold material (e.g., collagen). Collagen is a biocompatible material that has been widely used for biomedical applications. After collagen coating and crosslinking, dissolution of the sacrificial PCL cast resulted in a hollow shell of collagen in the shape of the original vascular cast. SEM images of the resulting vascular scaffolds showed a branching architecture similar to native organization (FIGS. 4A-4C). The inlet to the scaffold demonstrates that the structures were hollow where the PCL was removed (FIG. 4C). Cross-sectional and longitudinal histological sections stained with H&E also showed hollow, vessel-like structures within the scaffold with internal diameters as small as 20 µm (FIGS. 4D-4F). To demonstrate that these scaffolds represented a continuous and connected network, scaffolds were perfused with trypan blue dye and the distribution was recorded. FIGS. 4G-4I show images taken throughout the perfusion. These results demonstrate that biomimetic microvascular scaffolds can be created and used to pre-vascularize engineered tissue constructs.

Figure 6A:
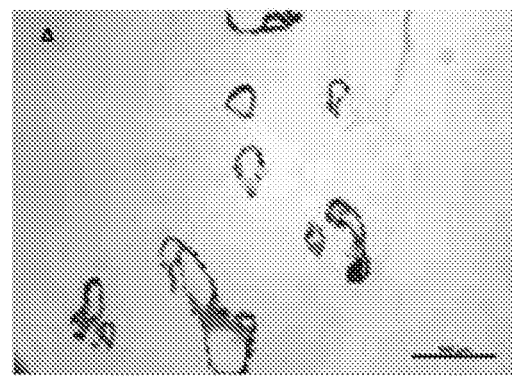
Figure 6B:
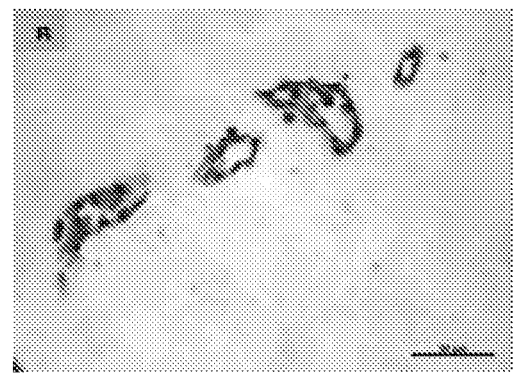
Figure 6G:
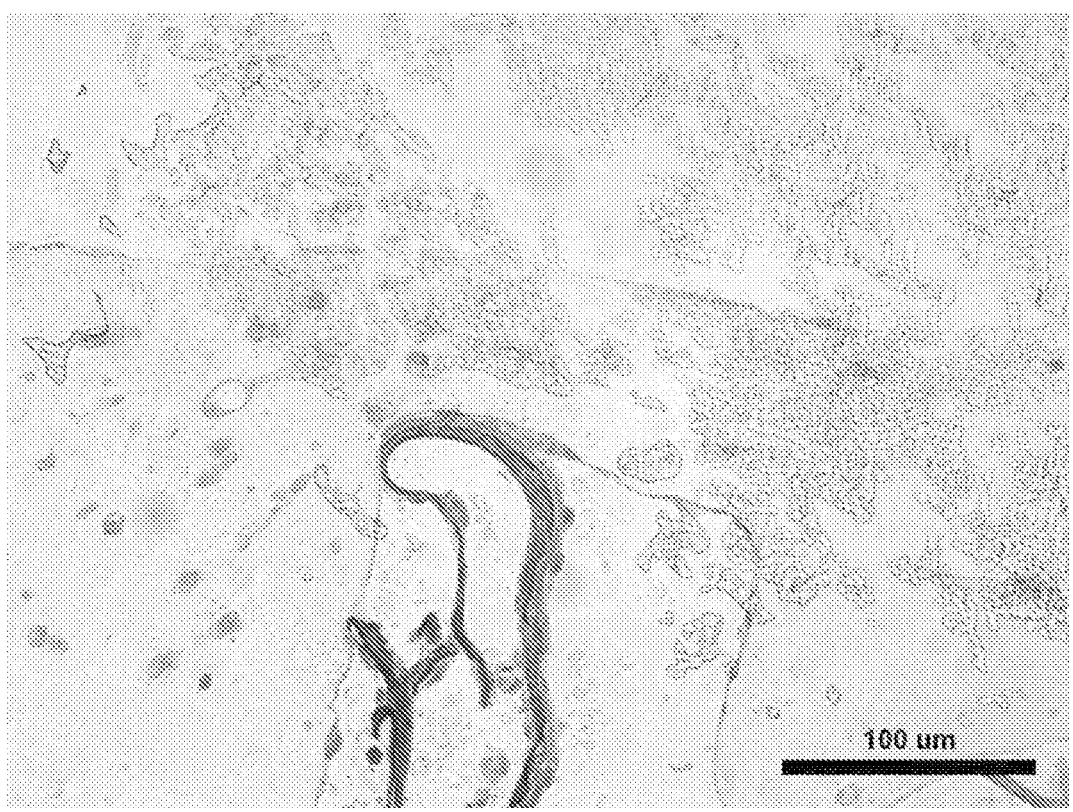

FIGS. 6A and 6B are histology images of a cell seeded collagen hydrogels. FIGS. 6A and 6B show an intact layer of endothelial cells around the vessel spaces created by the scaffold in the H & E images. FIG. 6A is a histology image of a cell seeded collagen hydrogel at 20× magnification, showing the endothelialization of a vascular scaffold. FIG. 6B is a similar image at 40× magnification. After 1 day in culture, the MS1 cells still formed an intact endothelium around the scaffolds. MS1 endothelial cell seeded vascular scaffolds were embedded and cultured in collagen hydrogels. A layer of endothelial cells was evident around the vessel spaces created by the scaffold in the H & E images. FIGS. 6C and 6D are histology images of endothelial cell seeded constructs cultured in collagen hydrogel for 1 day. After 1 day of culture, the endothelial cells are still well attached to the constructs. Both FIGS. 6C and 6D illustrate lumen of blood vessels in the constructs. Referring to FIGS. 6E and 6F, 1 day after embedding the endothelial seeded scaffolds in a collagen hydrogel, staining for the endothelial markers, VE-cadherin (FIG. 6E) and vWF (FIG. 6F) demonstrate a normal endothelial phenotype. The corner inserts in both FIGS. 6E and 6F show negative staining control. Referring to FIG. 6G, endothelial seeded constructs were embedded in a collagen hydrogel that contained human renal cells and cultured for 7 days. As shown in FIG. 6G, the start of renal tubular formation is visible and the lumen of the scaffold is visible with endothelial cells lining the scaffold.

EXAMPLE 3

Materials and Methods

Vascular Corrosion Casting of Kidney

Vascular corrosion casts were made of the left kidney of adult rats (Charles River). All animal procedures were performed in accordance with a protocol approved by the Institutional Animal Care and Use Committee at Wake Forest University. After euthanization of animals, the descending aorta and inferior vena cava were tied off above the renal artery. The aorta was cannulated with 50 g (I.D. 0.58 mm, O.D. 0.985 mm) tubing below the renal artery for perfusion. Batson's #17 Anatomical Corrosion Kits (Polysciences, Inc., Warrington, Pa.) were used to create standard casts according to the manufacturer's instructions. To create polycaprolactone (PCL, MW: 43,000-50,000) (Polysciences, Inc.) casts, the kidney was perfused with 1 mL of acetone (Warner Graham Company) and immediately perfused with 1 mL of 10% w/v PCL dissolved in acetone. The PCL-perfused kidneys were kept at room temperature for 24 h, transferred to 4° C. for 3 days to allow for acetone evaporation, and placed in 20% (w/v) sodium hydroxide for 48 h to digest the tissue. Washing in distilled deionized (DI) water for 24 h and additional rinsing was done to remove the digested tissue and reveal the vascular corrosion cast (FIGS. 2A and 2B, n=5). For microscopic analysis of the obtained casts, segments were sputter coated with gold (Anatech LTD Hummer 6.2) and imaged with a scanning electron microscope (SEM, Hitachi S-2600N). Using the SEM images, the glomerular sizes in 10% PCL and Batson 17 casts were quantified. The long axis of 5 randomly selected glomeruli on each kidney (n=3 per group) was measured using ImageJ software.

Fabrication of Collagen-Based Vascular Scaffolds

To fabricate collagen-based vascular scaffolds from the PCL cast, small segments of the cast were dip-coated with 9.8 mg/mL Type 1 rat tail collagen (BD Biosciences, San Jose, Calif.) and suspended for drying (FIG. 2C). After drying, the collagen-coated PCL cast was soaked in a crosslinking solution of 10 mM 1-ethyl-3-[3-dimethylaminopropyl]carbodiimide hydrochloride (EDC, Thermo scientific) and 10 mM N-hydroxysuccinimide (NHS, Aldrich) for 30 min. After the crosslinking process, warm acetone was used to remove the PCL casts from inside the collagen, leaving a hollow collagen vascular scaffold (FIG. 2D). The microstructure of the vascular scaffold was analyzed with SEM. To demonstrate the continuity of the hollow, vessel-like space, the vascular scaffolds were cannulated with a needle in the main artery. Trypan blue dye (Thermo Scientific) was perfused through the scaffold for contrast, and the perfusion was recorded through a light microscope (n=3).

Endothelialization of the Vascular Scaffolds

To test endothelialization of the vascular scaffolds, the green fluorescent protein (GFP)-transfected MS1 cell line (endothelial cell line derived from mouse pancreas, ATCC, Manassas, Va.) was used. MS1 cells were grown on standard cell culture plates in growth media consisting of DMEM/high glucose media (Thermo Scientific) supplemented with 10% fetal bovine serum (Thermo Scientific) and 1% antibiotic/antimycotic solution (Thermo Scientific) at 37° C. in 5% $CO_2$. The fabricated collagen vascular scaffolds were sterilized with ethanol before cell seeding, rinsed, and soaked in media for 10 min. Each scaffold was placed in one well on a 48 well plate. 200 µL of MS1 cell solution (10 million cells/mL) was added to each well. After a 25 min incubation, the cell-seeded scaffolds were placed into a new well to rest on the opposite side, and 200 µL of cell solution was added and allowed to incubate for 15 min. Seeded scaffolds were transferred to a final well and remained in growth media for culture at 37° C. in 5% $CO_2$. After 24 h, the cell-seeded scaffolds were imaged using an inverted fluorescent microscope (Zeiss Imager M1) to visualize GFP expression of the MS1 cells that had attached to the scaffold (n=3). For immunostaining, the seeded scaffolds were fixed with methanol, stained with a primary antibody for CD31 (rat anti-mouse CD31, MEC13.3, BD Pharmingen) and secondary antibody (goat anti-rat AF 594, Life Technologies), and counterstained with DAPI (Life Technologies) (n=2). Confocal images were acquired using Olympus Fluoview FV10i.

To test the feasibility of using the endothelialized vascular scaffold for the purpose of pre-vascularization in 3D tissue constructs, the MS1-seeded scaffolds were embedded in 2.4 mg/mL collagen gel (BD biosciences). To test the effect of embedding on scaffold integrity and ensure cell attachment, endothelialized scaffolds were embedded in 100 µL of neutralized collagen gel in a 96 well plate (n=3) and fixed immediately with 10% neutral buffered formalin (Leica Biosystems). And then, the gel with the endothelialized scaffold was paraffin embedded, sectioned into a 10 µm thickness, and stained with H&E. To evaluate short-term cell behavior (n=4), endothelialized scaffolds were also embedded in 48 well plates with 150 µL gel/well for 1 day. After the culture, the construct was paraffinembedded for H&E and immunohistochemistry. After antigen retrieval using citrate buffer (Polysciences, Inc.) and blocking process using a protein block agent (DAKO), the section was treated with primary antibody for VE-cadherin (Santa Cruz, 1:50 dilution) and subsequently with Alexa 594 labeled secondary antibody (Thermo Fisher Scientific), followed by nuclei staining with DAPI. For von-Willebrand Factor (vWF) immunostaining, the section was treated with a 1:50 dilution of anti-vWF (C-20) primary antibody (Santa Cruz) and 1:200 dilution of secondary antibody (Vector Laboratories, BA-5000) and then development with DAB treatment (Vector Laboratories). Finally, the sections were counterstained with hematoxylin.

Statistical Analysis

The mean glomerular length in PCL and Batson 17 vascular corrosion casts (n=3 casts, 5 replicates per cast) was compared using a two-tailed student's t-test.

Results

Casting Materials

The selection of appropriate casting materials was the first step toward fabrication of the vascular scaffolds. The commercially available Batson #17 kit was used as a positive control for comparison of novel casting materials. With the Batson #17 cast, the entire kidney was well perfused with casting solution, and the cast appears to be densely populated with vessels at the cortex (FIG. 5A). SEM analysis showed the preservation of the renal vascular network and the glomerular capillaries (FIG. 5B). While the Batson's #17 kit yields durable and precise vascular casts, it is not an appropriate sacrificial material due to crosslinking additives that prevent the cured polymethyl methacrylate (PMMA) casts from dissolving. Therefore, the Batson #17 kit cannot be used as a sacrificial casting material for this process; however, it serves as an appropriate standard for cast quality.

Corrosion casts made from 10% PCL showed uniform perfusion of the kidney but less dense structures of the cortex region (FIGS. 3A and 5I). SEM observation revealed preservation of most of the peritubular capillary structures, although some regions were truncated (FIG. 3B). This incomplete perfusion corresponded with the sparse appearance of the cast. PCL perfusion was able to reach the smallest capillaries as glomeruli are visible in the cast (FIG. 5J). The size of the glomeruli in the PCL casts was significantly (p=0.004) bigger than the glomeruli in the standard Batson #17 casts. The average long axis of the glomeruli in the PCL casts was 144.3±2.1 µl and the average length in Batson #17 casts was 101.9±12.5 µm.

The PCL was able to produce a cast that captured most of the vascular detail and was mechanically stable and readily soluble in acetone, making it the ideal sacrificial material. Other alternative casting materials were tested but failed to produce a complete cast or dissolve completely in compatible solvents. Additional materials tested included paraffin (FIGS. 5C-5D), PVC (FIGS. 5E-5F), gallium (FIGS. 5G-5H), alginate (data not shown), and Pluronic 127 (data not shown).

Fabrication of Vascular Scaffolds

To fabricate hollow-structured vascular scaffolds from the PCL casts, the casts were coated with collagen solution, cross-linked, and treated with acetone to remove the PCL. Under SEM observation, the resulting collagen-based vascular scaffolds showed the same 3D branching architecture that was visible in the corrosion casts (FIGS. 4A-4C). The arterial inlet for the scaffold was visibly hollow (FIG. 4C, dotted line). To demonstrate that the visible hollow spaces were connected and continuous, the scaffolds were perfused with blue dye. FIGS. 4G-4I illustrate the progression of the dye through the scaffold during perfusion. The dye perfused into the single arterial inlet and diverged equally at each branching point. This demonstrated that the vascular scaffold maintained mechanically stable, hollow, branching structures that could allow perfusion similar to native blood vessels.

Endothelialization of the Vascular Scaffolds

Figure 8A:
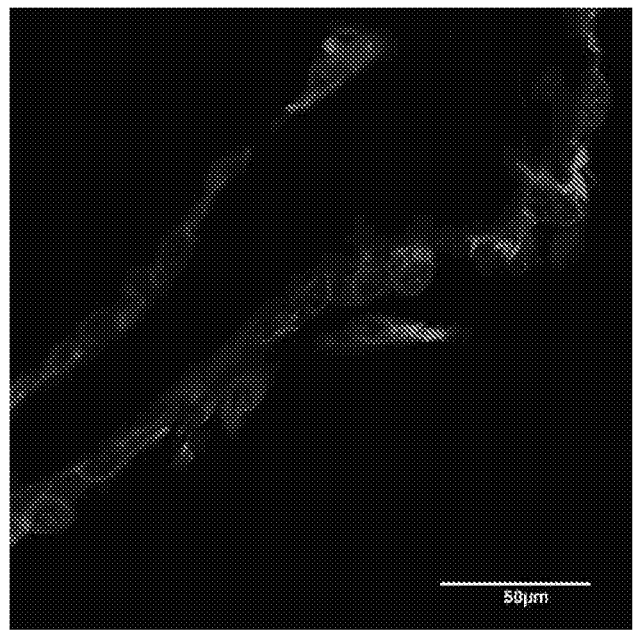
FIGS. 8A-8B illustrate confocal images of endothelial cells on scaffolds before embedding in a hydrogel. Representative confocal images of the endothelialized scaffolds stained for CD31 and counterstained with DAPI showed well-aligned endothelial morphology and CD31 expression and demonstrated maintenance of an endothelial-specific phenotype on the vascular structures. Complete vessel coverage was apparent in transverse sections (FIG. 8A, 600×, scale: 50 µm) and cross sections (FIG. 8B, 600×, scale: 50 µm).
Figure 8B:
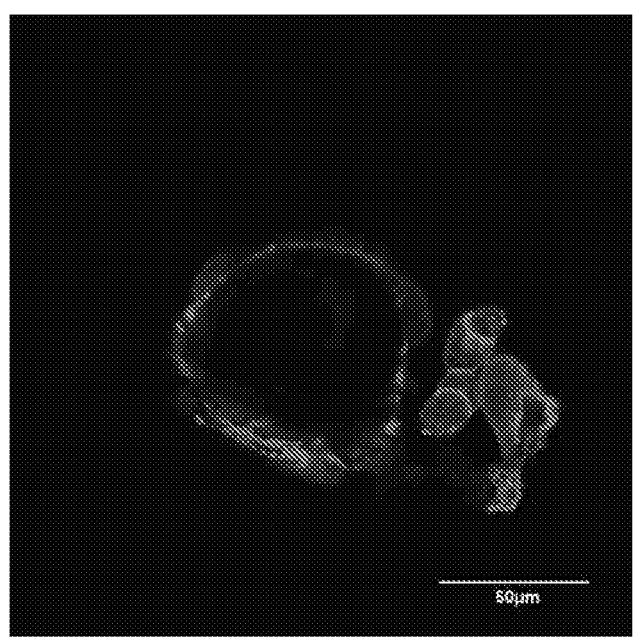
Figure 9A:
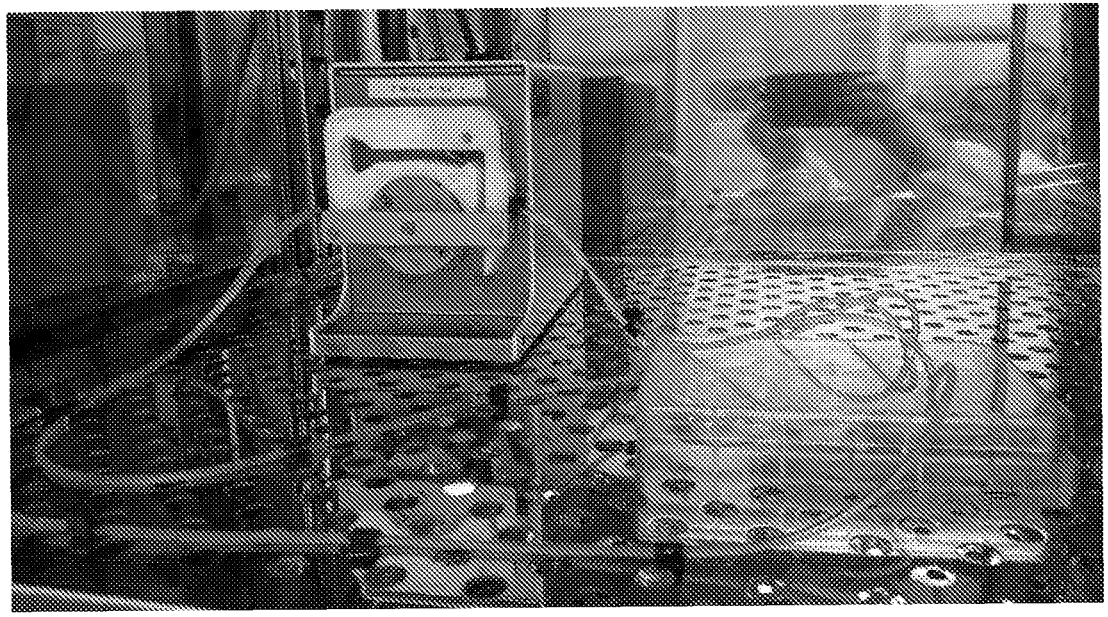
FIGS. 9A-9B illustrate a bioreactor used to test the functionality of the scaffolds of the present invention using silicone inserts placed inside a six-well plate.
Figure 9B:
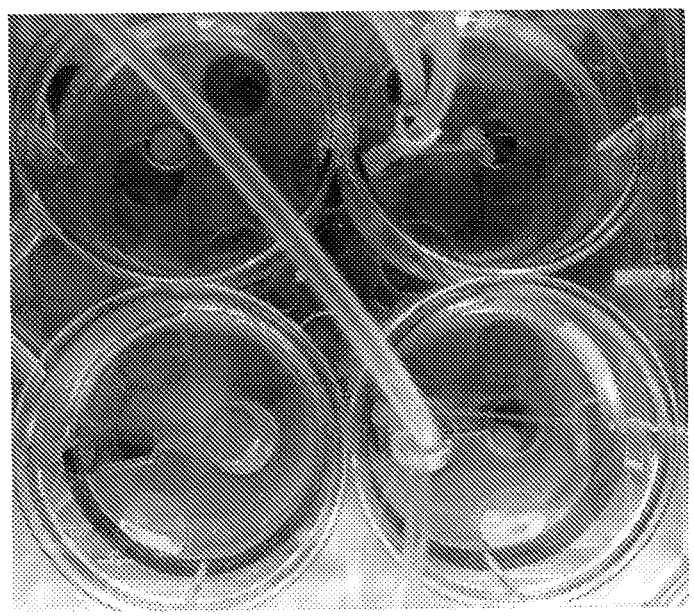

Endothelialization of the vasculature within a construct is critically important. To test the feasibility of forming an endothelial layer on the vascular scaffold, the scaffold was seeded with MS1 cells expressing GFP for visualization. After 24 h, the entirety of each scaffold was seeded with a layer of cells (FIG. 7C-7D). No background was observed from the unseeded collagen scaffold (FIGS. 7A-7B). Confocal images of staining for the endothelial marker, CD31, on vessel cross-sections showed normal endothelial cell morphology with complete and uniform endothelial cell coverage (FIGS. 8A-8B).

To test how the microvascular scaffold can be used for the purpose of pre-vascularization within 3D tissue constructs, the endothelialized scaffolds were embedded in collagen gels to mimic potential incorporation into tissue-engineered constructs. The collagen gel easily surrounded the scaffolds. The hollow, vessel-like spaces remained free of hydrogel and endothelial cells were not dislodged during embedding. H&E staining showed consistent endothelial coverage around the hollow, vessel-like structures formed by the vascular scaffold and collagen gel was not observed inside the lumens (FIGS. 6A and 6B). The cross-linked collagen scaffolds with endothelialization are defined by the relatively darker areas of eosin staining indicated as arrows. During 1 day of static culture in the collagen gels, intact endothelial cell layers were confirmed by H&E staining and immunostaining of longitudinally cross-sectioned vessels (FIGS. 6C-6F). The immunostaining for the endothelial cell markers such as VE-cadherin and von Willebrand factor (vWF) (FIGS. 6E and 6F, respectively), show that the endothelial cells maintained their phenotype during the culture.

Discussion

Replacement of volumetric pieces of diseased or damaged tissues or organs remains a critical unmet need in the clinical setting. Engineering of functional 3D tissue constructs is severely hindered by limited methods of pre-vascularization. Current technology offers fabrication of vessel networks through endothelialization of simple branching tubes in two or three dimensions, yet these structures fail to replicate native vasculature. Therefore, this study aimed to create a pre-vascularization technique that captures the complexity of native vessels. Using vascular corrosion casts of healthy native kidneys, a biomimetic vascular scaffold was produced that remained perfusable and that could be endothelialized, and was confirmed by electron microscopic and histological analysis. This method of pre-vascularization eliminated the need for specialized equipment and higher costs associated with other methods.

In the fabrication of our microvascular scaffolding, the selection of appropriate sacrificial vascular corrosion casting material is critically important to success (FIGS. 2A and 2B). Traditionally, vascular corrosion casts are meant to be stable and durable to study vascular anatomy. Here, a sacrificial vascular cast was created that served as a sacrificial template during the scaffold creation process and utilized an appropriate corrosion casting material. In general, casting materials needed to be liquid to allow efficient infusion through the entire vasculature and later solidify once inside the vessels. Additionally, they needed to tolerate tissue digestion by sodium hydroxide (NaOH). Finally, the casting material must dissolve or return to a liquid state after being coated with the scaffold material, at which time a solvent can be used to flush the casting materials from inside the scaffold materials. The casting material criteria were based on creating single use casts. Alternatively, a two-part permanent mold could be made of a segment of vascular corrosion cast and used to replicate that piece over and over, rather than recasting a new organ each time. For kidney casting, organ isolation and perfusion is straightforward and repeatable, and multiple scaffolds can be created from a single organ by dividing the cast into segments.

Various types of casting materials were considered and tested. Natural materials like gelatin and fibrin based gels would not survive the tissue digestion process. Gels like Pluronic F127 and alginate were not strong enough to maintain the shape of a vascular cast. Paraffin was used, but was too soft to withstand the processing and further handling of the scaffold creation method. Some materials were unable to perfuse the organ completely, such as Gallium. Various types of synthetic materials have been considered as casting material candidates and included poly-(lactic acid) (PLLA), poly-(lacticglycolic acid) (PLGA), and polycaprolactone (PCL). PCL was chosen because it readily dissolved in alcohol solvents and allowed for easy perfusion and removal. Based on the gross images (FIGS. 5A-5K), PCL was able to perfuse evenly into the kidney, but did not fill the entire vascular network. Although some areas of smaller vessels were truncated, the PCL was able to occasionally perfuse into the smallest capillaries to preserve the glomerular structures. The retained glomerular and capillary structures were confirmed by SEM analysis (FIG. 5J). Although PCL does not produce a corrosion cast with the same level of detail as a commercial kit, it performed the best out of the tested casting materials. The size of the glomeruli in PCL casts were quantified and found to be approximately 50% longer than the glomeruli in normal Batson #17 casts, which was attributed to the possibility that the pressure during PCL perfusion could be higher than that during Batson perfusion, causing the glomeruli to expand.

Once the vascular cast is created, the next step required the incorporation of materials with the cast to fabricate vascular scaffolds with hollow vascular structures. Since the chosen casting material was a plastic (PCL), scaffold materials composed of synthetic polymers were not ideal since organic solvents that dissolve the polymers can damage the PCL cast during the coating process. Therefore, naturally derived polymers were considered to be appropriate scaffold materials. Natural polymers needed to be biocompatible, biodegradable, and mechanically stable to yield a vascular scaffold for in vitro cell culture and in vivo implantation. Several types of natural polymers have been used as scaffolding materials in tissue engineering. Among several materials, chitosan was tested, which enabled formation of vascular scaffolds. However, the scaffolds were not robust enough to withstand handling during processing and cell culture (data not shown). Conversely, collagen-based scaffolds were easy to handle and preserved the 3D architecture, as confirmed by SEM analysis and dye perfusion test (FIGS. 4A-4C and 4G-4I). Crosslinking of collagen molecules after coating the PCL cast was critically important to maintain 3D vascular structures. EDC/NHS crosslinking formed amide bonds between carboxyl and amine groups on the collagen fibers. This crosslinking is a commonly used method with the benefits of using a zero-length crosslinker and having good biocompatibility. Crosslinking the collagen improved the collagen's ability to maintain 3D structures, but also decreased its susceptibility to enzymatic degradation. Based on our results, it was possible to create a collagen vascular scaffold that copied the native vascular network in a healthy rat kidney.

To be functional, the vascular structures require a lining of endothelial cells to facilitate the movement of oxygen, nutrients and waste. Additionally, endothelial cell coverage prevent thrombosis during blood perfusion following implantation. The continuous and homogeneous endothelialization of collagen based vascularized structures are demonstrated in FIGS. 7A-8B, where the endothelialization retained endothelial specific phenotypes, confirmed by CD31 immunostaining (FIGS. 8A-8B). The incorporation of the endothelialized vasculatures into the 3D culture system was confirmed by histological analysis (FIGS. 6A-6F) during 1 day of culture. Perfusion of an endothelialized scaffold with fresh media in vitro can support cell viability in a large hydrogel construct. Also, a heterogeneous mix of adult renal cells can self-assemble to form tubule-like structures in hydrogels.

By creating a vascular scaffold in the proposed manner, there are additional advantages over the current fabrication techniques. The developed techniques in this study were technically simple and cost-effective; moreover, they were quite novel among current techniques for the production of vascular networks for tissue constructs. In this study, the feasibility of creating vascular scaffolds using a small tissue sample (rat kidney) was demonstrated. This same technique can be applied to larger organs without modification; and it fulfills a critically important aspect for translation into clinical trials. The scalability of this technique enhances the innovative nature of this study. Furthermore, this technique can be applied easily to any tissue or organ regardless of the vascular architecture. In addition, combining a hydrogel-based tissue construct with a pre-formed vascular scaffold allows for the use of many established culture systems. For example, myoblasts and C2C12 cells have been shown to form multinucleated muscle fibers in fibrin gels. The incorporation of a vascular network would allow for the creation of larger constructs by providing oxygen, and the scaffold itself may facilitate the developing tissue. Previously, aligned 3D scaffolds were shown to positively influence muscle fiber formation by cultured myoblasts. A vascular scaffold composed of aligned, parallel blood vessels could provide similar feedback and promote orientation of cells and muscle fiber formation.

Gross and SEM analysis revealed glomerular structures were retained within PCL casts; however, the number of glomeruli and capillary structures appeared to be fewer than the number observed in the positive cast control (Batson's kit) (FIG. 5). Similarly, the collagen-based vascular scaffold showed loss of capillary structures. Optimization of the casting and scaffold creation processes is needed. Development of this technology will require the ability to completely remove the collagen scaffold material from the lumen of the vessel structures. In this study, the endothelial cells were seeded on the outside of the vascular scaffold. While cell attachment and the formation of an endothelium layer was demonstrated, this method of seeding left a layer of collagen in the lumen of the vessel. Further long-term examination of the endothelialized scaffolds will be necessary to evaluate whether the endothelial cells can digest the collagen scaffold, resulting in the eventual formation of an empty lumen. The EDC/NHS crosslinking of the vascular scaffold may slow the degradation of the collagen. If removal of the scaffold by cell digestion is not sufficient, perfusion of collagenase solutions could be used to expedite removal. An additional option for creating implantable constructs would be to seed the endothelial cells internally through perfusion. Perfusion seeding technique has been used successfully with other pre-vascularized strategies, but with very complex vascular scaffolds or in the case of very small capillary structures, this method may not be ideal.

CONCLUSIONS

Volumetric tissue engineered constructs require prevascularization to support cell viability and promote tissue formation. To date, pre-vascularization techniques have produced simple, 3D structures; although, existing techniques fail to reproduce the native vascular features and often require expensive and specialized equipment. In this study, a novel method for creating a microvascular scaffold that exploits vascular corrosion casts as a template was developed. This method can be used to create simple, cost effective, biomimetic microvascular scaffolds for pre-vascularization of 3D engineered tissue constructs. The results demonstrate that these microvascular scaffolds were able to support endothelialization and promoted the incorporation of hydrogel-based constructs. The tissue-specific nature of this process can be applicable to a broad range of tissue-engineered constructs.

The teachings of all patents, published applications and references cited herein are incorporated by reference in their entirety.

While the preferred embodiments of the invention have been illustrated and described, it will be clear that the invention is not so limited. Numerous modifications, changes, variations, substitutions, and equivalents will occur to those skilled in the art without departing from the spirit and scope of the present invention as defined by the appended claims.

What is claimed:

1. A method of creating a three-dimensional, hollow vascular scaffold comprising:
   obtaining a sample comprising native tissue with an internal vasculature;
   perfusing a sacrificial internal casting composition into the native tissue vasculature;
   solidifying the sacrificial internal casting composition within the native tissue vasculature;
   digesting the native tissue, thereby creating a sacrificial solid cast of the native tissue vasculature;
   coating the sacrificial solid cast of the native tissue vasculature with a durable biocompatible outer scaffold material that surrounds the sacrificial solid cast of the native tissue vasculature;
   removing the sacrificial solid cast, thereby forming a three-dimensional, hollow vascular scaffold with a branching 3D network of hollow vessel-like tubes that mimics the original vasculature of the native tissue; and
   seeding the scaffold with a population of endothelial or endothelial progenitor cells.

2. The method of claim 1, wherein the sacrificial internal casting composition comprises polycaprolactone.

3. The method of claim 2, wherein the sacrificial internal casting composition is a solution comprising about 5% to about 30% polycaprolactone.

4. The method of claim 1, wherein the sacrificial internal casting composition comprises gallium.

5. The method of claim 1, wherein the durable biocompatible outer scaffold material comprises collagen.

6. The method of claim 1, wherein the step of digesting the native tissue further comprises digesting the native tissue surrounding the sacrificial solid cast.

7. The method of claim 1, wherein the step of digesting the native tissue further comprises enzymatic digestion of the native tissue surrounding the sacrificial solid cast.

8. The method of claim 1 wherein the step of removing the sacrificial solid cast further comprises dissolving the sacrificial solid cast with a solvent.

9. The method of claim 8, wherein the solvent is an organic solvent.

10. The method of claim 1 wherein the step of removing the solid cast further comprises raising a temperature of sacrificial solid cast to liquefy the sacrificial solid cast.

11. The method of claim 1, further comprising seeding an internal surface, an external surface, or a combination thereof of the three-dimensional, hollow vascular scaffold with said population of endothelial or endothelial progenitor cells.

12. The method of claim 11, wherein the population of cells comprises endothelial cells.

13. The method of claim 11, wherein the population of cells comprises endothelial progenitor cells.

14. The method of claim 1, further comprising embedding the three-dimensional vascular scaffold in a hydrogel.

15. The method of claim 14, wherein the hydrogel comprises a population of cells.

16. The method of claim 14, wherein the population of cells comprises skeletal muscle cells, smooth muscle cells, fibroblasts, renal cells, hepatocytes, pancreatic islet cells or beta-cells, smooth muscle cells or combinations thereof.

17. A three-dimensional, hollow scaffold having a branching 3D network of hollow vessel-like tubes that mimics the original vasculature of native tissue comprising:
   a durable external scaffold layer on a portion of vascular corrosion cast;
   wherein the durable external scaffold layer comprises a biocompatible material that promotes endothelial cell or endothelial progenitor cell seeding and is formed by perfusing a sacrificial internal casting composition into a tissue vasculature; solidifying the sacrificial internal casting composition within the native vasculature; digesting the native vasculature, thereby creating a solid cast of the native vasculature; coating the solid cast with a biocompatible outer casting material; and removing the sacrificial internal casting composition thus forming a three-dimensional, hollow scaffold having a branching 3D network of hollow vessel-like tubes that mimics the original vasculature of native tissue.

18. The scaffold of claim 17, wherein the biocompatible material comprises collagen or chitosan.

19. The scaffold of claim 17, wherein the biocompatible material forms a biomimetic scaffold of at least one of a renal vasculature, a gastrointestinal vasculature, a nervous system vasculature, a pulmonary vasculature, a cardiac vasculature, a hepatic vasculature, a splenic vasculature, a pancreatic vasculature, or a musculoskeletal vasculature.

20. The scaffold of claim 19, wherein the population of cells comprises endothelial cells or endothelial progenitor cells.

21. The scaffold of claim 17, wherein the scaffold is seeded with a population of cells onto an internal surface, an external surface, or a combination thereof of the scaffold.

\* \* \* \* \*